(12) United States Patent
Gorski et al.

(10) Patent No.: US 6,622,034 B1
(45) Date of Patent: Sep. 16, 2003

(54) OXIMETER SENSOR WITH FUNCTIONAL LINER

(75) Inventors: Stephen H Gorski, Eagle, WI (US); Alfred J Kelly, Fond Du Lac, WI (US)

(73) Assignee: Imagenix, Inc., Eagle, WI (US)

( * ) Notice: Subject to any disclaimer, the term of this patent is extended or adjusted under 35 U.S.C. 154(b) by 0 days.

(21) Appl. No.: 10/070,016

(22) PCT Filed: Sep. 8, 2000

(86) PCT No.: PCT/US00/24569
§ 371 (c)(1),
(2), (4) Date: Jul. 31, 2002

(87) PCT Pub. No.: WO01/17426
PCT Pub. Date: Mar. 15, 2001

Related U.S. Application Data
(60) Provisional application No. 60/153,346, filed on Sep. 10, 1999.

(51) Int. Cl.[7] .................................................. A61B 5/00
(52) U.S. Cl. ...................................... 600/344; 600/310
(58) Field of Search ................................ 600/310, 322, 600/323, 340, 344

(56) References Cited

U.S. PATENT DOCUMENTS

| | | |
|---|---|---|
| 2,706,927 A | 4/1955 | Wood |
| 2,951,200 A | 7/1960 | Critchlow |
| 3,167,658 A | 1/1965 | Richter |
| 3,439,258 A | 4/1969 | Van Leeuwan |
| 3,531,978 A | 10/1970 | Yeager |
| 3,535,637 A | 10/1970 | Goransson |
| 3,599,629 A | 8/1971 | Gordy |
| 3,602,213 A | 8/1971 | Howell |
| 3,638,640 A | 2/1972 | Shaw |
| 3,704,706 A | 12/1972 | Herczfeld et al. |
| 3,720,199 A | 3/1973 | Rishton et al. |
| 3,740,533 A | 6/1973 | van Zeggelaar |
| 3,757,217 A | 9/1973 | Pearson |
| 3,769,974 A | 11/1973 | Smart et al. |
| 3,807,388 A | 4/1974 | Orr et al. |
| 3,819,276 A | 6/1974 | Kiess et al. |
| 3,833,864 A | 9/1974 | Kiess et al. |
| 3,847,483 A | 11/1974 | Shaw et al. |
| 3,880,006 A | 4/1975 | Poduje |
| 3,905,229 A | 9/1975 | Togo et al. |
| 3,910,701 A | 10/1975 | Henderson et al. |
| 3,943,440 A | 3/1976 | Edwards |
| 3,976,150 A | 8/1976 | Wilson et al. |
| 3,998,550 A | 12/1976 | Konishi et al. |
| 4,000,643 A | 1/1977 | Pearson |
| 4,013,067 A | 3/1977 | Kresse et al. |
| 4,038,532 A | 7/1977 | Burris et al. |

(List continued on next page.)

FOREIGN PATENT DOCUMENTS

| | | |
|---|---|---|
| CA | 671279 | 10/1963 |
| DE | 3100610 | 7/1982 |
| EP | 0019478 | 5/1980 |
| EP | 0 329 196 | 8/1983 |
| FR | 1589461 | 3/1970 |
| FR | 2262952 | 10/1975 |

OTHER PUBLICATIONS

US 4,928,691, 5/1990, Nicolson et al. (withdrawn)
US 4,928,691, 5/1990, Nicolson et al. (withdrawn).

*Primary Examiner*—Eric F. Winakur
(74) *Attorney, Agent, or Firm*—Factor & Partners (57) ABSTRACT

This invention is an improve non-invasive electro-optical sensor probe (10) that is initially L shaped to provide a mechanical means for accurate positioning of the sensor for subsequent use in connection with a patient appendage. The sensor further includes a leveling pad for at least partially surrounding a protruding sensor element (22, 24) to minimize protrusion of the element into the skin of a patient, and a functional liner (18) for use in pretest of the sensor prior to positioning on a patient.

9 Claims, 5 Drawing Sheets

U.S. PATENT DOCUMENTS

| | | |
|---|---|---|
| 4,059,991 A | 11/1977 | Dybel et al. |
| 4,064,396 A | 12/1977 | Pannarello |
| 4,082,998 A | 4/1978 | Marriott |
| 4,086,915 A | 5/1978 | Kofsky et al. |
| 4,091,803 A | 5/1978 | Pinder |
| 4,167,331 A | 9/1979 | Nielsen |
| 4,179,745 A | 12/1979 | Wuertele |
| 4,192,005 A | 3/1980 | Kurtz |
| 4,218,916 A | 8/1980 | Mutziger |
| 4,225,410 A | 9/1980 | Pace |
| 4,263,803 A | 4/1981 | Burkhardt |
| 4,266,554 A | 5/1981 | Hamaguri |
| 4,282,578 A | 8/1981 | Payne et al. |
| 4,290,297 A | 9/1981 | Anderson |
| 4,305,401 A | 12/1981 | Reissmueller et al. |
| 4,323,972 A | 4/1982 | Winter |
| 4,331,026 A | 5/1982 | Howard et al. |
| 4,337,638 A | 7/1982 | Leonard et al. |
| 4,349,886 A | 9/1982 | Ibar |
| 4,350,165 A | 9/1982 | Striese |
| 4,362,935 A | 12/1982 | Clark, III |
| 4,370,984 A | 2/1983 | Cartmell |
| 4,380,240 A | 4/1983 | Jobsis et al. |
| 4,406,289 A | 9/1983 | Wesseling et al. |
| 4,407,272 A | 10/1983 | Yamaguchi |
| 4,407,290 A | 10/1983 | Wilber |
| 4,407,298 A | 10/1983 | Lentz et al. |
| 4,446,715 A | 5/1984 | Bailey |
| 4,481,804 A | 11/1984 | Eberhard et al. |
| 4,494,550 A | 1/1985 | Blazek et al. |
| 4,621,643 A | 11/1986 | New, Jr. et al. |
| 4,700,708 A | 10/1987 | New, Jr. et al. |
| 4,770,179 A | 9/1988 | New, Jr. et al. |
| 4,830,014 A | 5/1989 | Goodman et al. |
| 4,865,038 A * | 9/1989 | Rich et al. .................. 600/344 |
| 4,867,165 A | 9/1989 | Noller et al. |
| 5,054,488 A | 10/1991 | Muz |
| 5,058,588 A | 10/1991 | Kaestle |
| 5,217,012 A | 6/1993 | Young et al. |
| 5,368,025 A | 11/1994 | Young et al. |
| 5,429,129 A | 7/1995 | Lovejoy et al. |
| 5,638,818 A | 6/1997 | Diab et al. |
| 5,830,136 A | 11/1998 | Delonzor et al. |
| 5,891,021 A | 4/1999 | Dillon et al. |

* cited by examiner

OXIMETER SENSOR WITH FUNCTIONAL LINER

This application claims the benefit of provisional application No. 60/153,346 filed Sep. 10, 1999.

BACKGROUND OF THE INVENTION

The present invention relates generally to a sensor for transillumination of a blood-perfused portion of flesh to measure light extinction during transillumination, or transmissive pulse oximetry. More particularly, the present invention relates to a disposable oximeter sensor having a mechanical means for pretest of the disposable oximeter sensor and a mechanical means for improved positioning of the sensor.

Disposable oximeter sensors have been developed and used in the clinical setting for several years. During patient treatment, an oximeter sensor is used to monitor the oxygen saturation level in blood perfused tissue. Typically, oximeter sensors comprise a light source, such as a light emitting diode, a photo-sensor located such that a portion of the light emitted from the light source is received by the photo-sensor, and a means for securement to the patient. An example of an oximeter sensor has been disclosed in U.S. Pat. No. 4,830,014 granted to Goodman et al. As disclosed therein, a non-invasive, electrooptical sensor probe includes a flexible, initially substantially planar, web-like, support structure having a light source and a photo-sensor mounted in the web. An adhesive layer is further provided for removably adhesively securing the device to a portion of a patient's skin. While this type of sensor has been used in clinical settings, difficulty in positioning the sensor has been observed in practice. With an initially planar configuration and no assisting structural positioning elements, it is difficult to achieve proper alignment of the light source with the photo-sensor. Further, the optical elements present within the sensor protrude somewhat into the plane of the tape in contact with the patient's skin. Over a period of time, a dent in the skin surface may cause skin discomfort or even pressure necrosis in sensitive skin, such as that of a neonate.

Another sensor is disclosed in U.S. Pat. No. 5,217,012 granted to Young et al. The device disclosed in this patent includes a U-shaped support structure having spaced, opposed upper and lower inner surfaces. The U-shaped structure is designed to aid in pre-alignment of the device during patient use. A light source and a photosensor are mounted in the U-shaped support structure. The sensor includes means, such as adhesive, for removably securing the sensor to the skin. In practice, devices similar to that disclosed in the above-mentioned patent have proved to be predisposed to accidental closure of the U-shaped support structure upon itself, adhesive to adhesive, during application. This creates difficulty for the clinician, and nullifies the positioning feature of the U-shaped support structure taught by the Young patent.

It should be further noted that, in general, the production of disposable oximeter sensors is, by economic necessity, not of the same grade as more expensive reusable devices, such as finger clip-type sensors. This is due to the high-volume production means used-in the manufacture of disposable devices, such as the lower sampling and verification programs employed in product testing, as compared to reusable devices. However, the benefits of a disposable device, including size, application benefits, and advantages for infection control, cause the disposable product to be preferred by many health care professionals. Furthermore, despite medical quality system improvements to reduce the number of sensor failures that reach the patient care environment, the predominant type of sensor failure is "out of the box" failure of newly applied sensors. This type of failure is especially problematic as it may cause a gap in patient care and loss of valuable time while the performance deficiency is investigated or a replacement sensor is located and applied. This situation may be further complicated in treating patients having compromised circulation, where readings are more difficult to obtain.

SUMMARY OF THE INVENTION

In view of the above-noted concerns, and also to present a sensor for transillumination of a blood-perfused portion of flesh that is easily positioned, minimally invasive to the patient, and able to be pretested, the present invention teaches a novel oximeter sensor. The present invention contemplates an initially L-shaped sensor having positioning elements and a removable liner. The sensor may be disposable, or for single patient use, and is designed to be affixed to any blood-perfused tissue, preferably a fingertip.

The sensor includes a flexible support structure having outer and inner surfaces, at least one positioning element, a light source, a photo-sensor, a conformal adhesive tape laminate mounted on the support structure, a leveling pad, and a removable liner. The inner surface of the flexible support structure preferably includes a biologically acceptable adhesive for adjacent retention of the adhesive tape laminate and adhesion to the skin surface while the sensor is in use.

The present invention contemplates an adhesive tape laminate, which is adhesively mounted on the adhesive coated, inner surface of the support structure. The conformational adhesive tape laminate is preferably comprised of an adhesive coated, longitudinally folded, adhesive tape. The tape laminate preferably includes an outer, light transmissive layer. The longitudinally folded tape laminate is defined by two oppositely disposed outer surfaces and two, facing inner surfaces, with a fold pocket area located between the two facing, inner surfaces. A light source and a photo-sensor are mounted in the fold pocket area in a spaced-apart configuration so that they may be positioned generally opposite each other upon mounting of the sensor to an appendage, such as a finger. One of the outer surfaces of the tape laminate is preferably provided with at least one window area. The window area is created when a portion of an inner surface is removed, leaving only the outer, light transmissive layer. At least one of the optical elements extends inwardly of the window area, thereby permitting light to pass therethrough.

The sensor according to the present invention is further provided with at least one positioning element. The positioning element is provided to cause the sensor to maintain a generally L-shape prior to use. The positioning element is preferably located in the fold pocket area of the tape laminate, at a location approximately midpoint of the laminate longitudinal length, but preferably somewhat closer to the photo-sensor. This arrangement ensures that the sensor is defined by two unequal leg portions when the sensor is in its initial L shape. However it is to be understood that the positioning element may be located at any point along the tape laminate length that will allow a generally L-shape to be imparted to the attached support structure and tape laminate. The positioning element is relatively stiff to impart an initially generally L-shape to the sensor and its cooperating elements, and permits the clinician to accurately position and apply the sensor to patient tissue up to the bend of the L, thereby locating the sensor elements in proper opposition once the device is secured in operating position. This feature overcomes the difficulties encountered with the U-shaped sensors presently in use, such as premature adhering prior to proper positioning.

The sensor of the present invention is further provided with a leveling means positioned in the fold pocket area in the marginal area surrounding at least a major portion of the optical sensor element. The leveling means is preferably a thin, deformable material such as a PVC foam tape approximately the thickness of the optical elements. The leveling means allows the sensor to conformably match the contours of the skin and helps alleviate protrusion of the optical sensor elements into the skin of the patient. This feature is of particular importance in conditions of long term monitoring in which the sensor is to be used for several days, or in which the sensor is to be applied to fragile skin, in the case of neonates. Furthermore, the leveling means provides an additional purpose in improving the seal between the skin and the optical sensor element. As a result, incident stray light that may impinge on the optical sensor element is reduced. This feature improves the sensor'performance with respect to patient motion in which stray light may produce an extraneous signal.

The present invention further contemplates an oximeter sensor having an adhesively attached liner. The liner is initially attached to the inner adhesive surface of the flexible support structure, but may be easily peeled away from the support structure to allow the sensor to be mounted to a patient appendage. The liner includes two end portions, which may be adapted to conjoin, forming a tear drop shape. When the liner presents the tear drop configuration, the light source and the photo-sensor are presented in opposition to one another allowing the clinician to test the performance of the sensor prior to removal of the liner and attachment of the sensor to the patient. Alternatively, this arrangement, in configuration with the functional liner, may be used to test the performance of the sensor at the manufacturing site, as a quality assurance prior to shipping. The liner is preferably substantially transparent to the wavelengths of light used by the sensor for interrogation of patient tissue. These features permit sensor verification and system performance evaluation prior to use, thus increasing the likelihood of successful patient monitoring.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

The present invention is directed to an improved sensor for transillumination of a blood-perfused portion of flesh having mechanical positioning and pretest means that is adapted to be applied to the skin of a patient (see FIGS. 5–7) needing blood oxygen level monitoring. The improvement resides principally in the initially, substantially L-shape of the sensor, as provided by positioning elements, the leveling means and the means for pretesting the optical elements.

Figure 1:
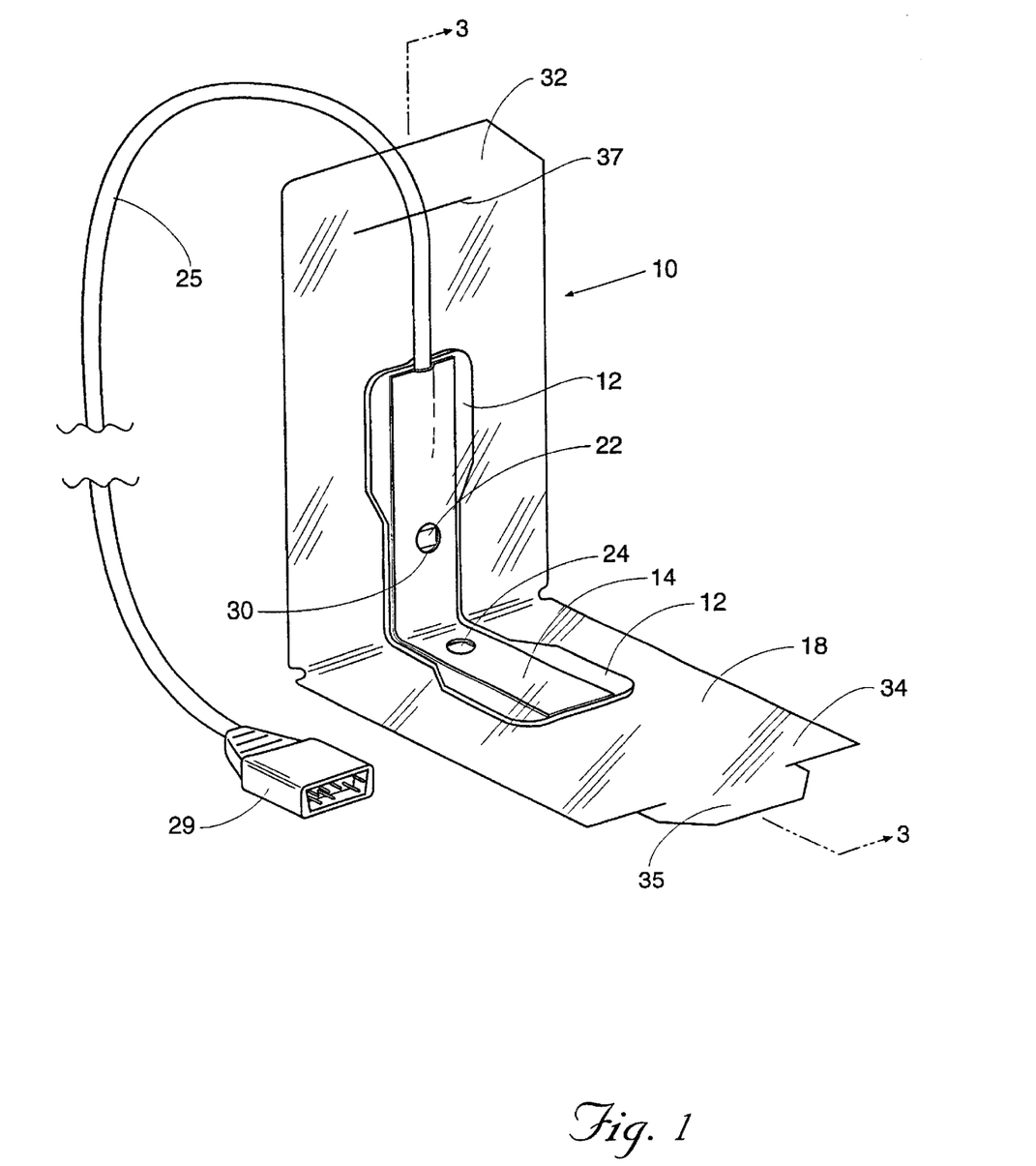
FIG. 1 is a perspective view of the oximeter sensor of the present invention showing the sensor in its initial L-shaped configuration prior to being applied on a patient appendage.
Figure 2:
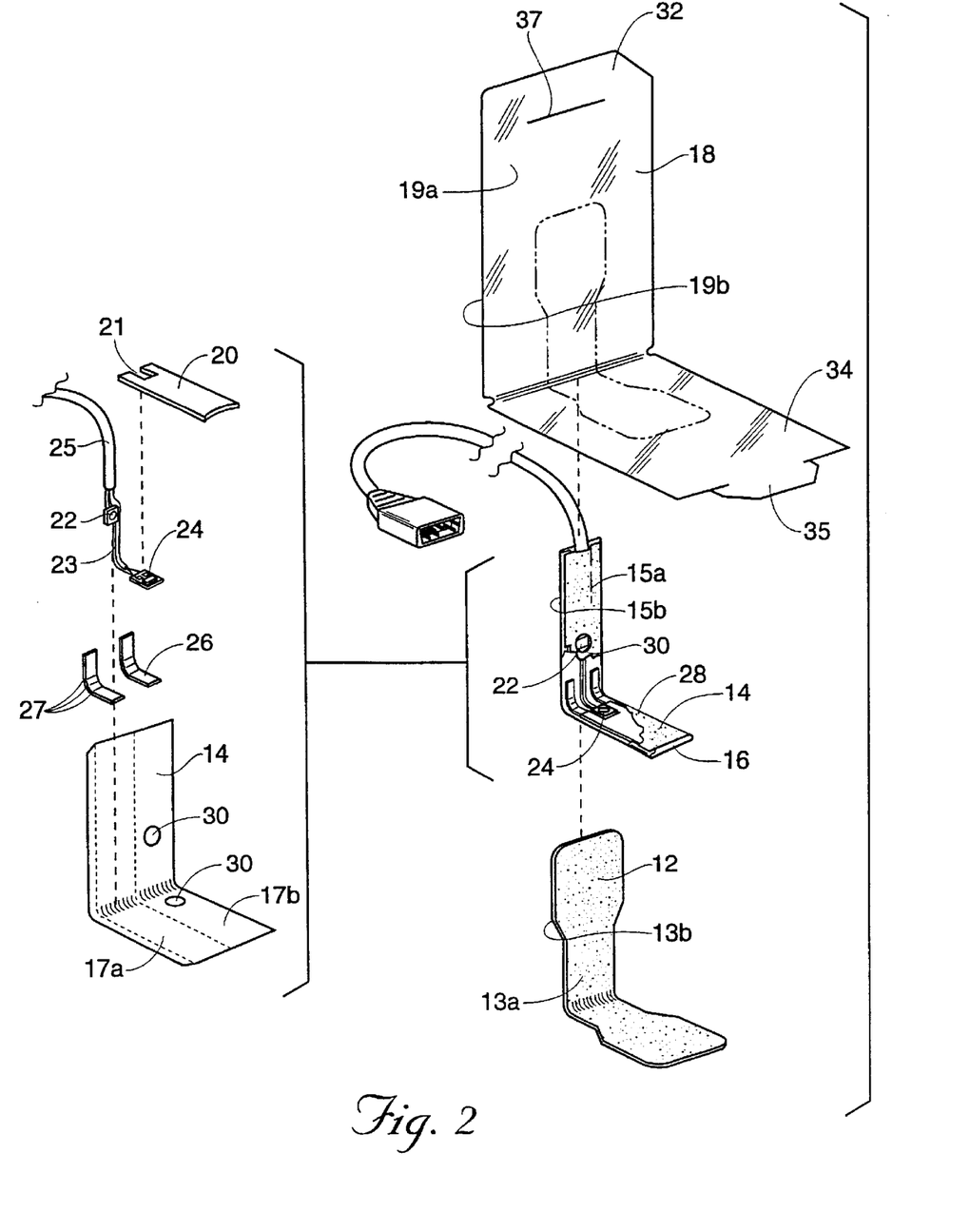
FIG. 2 is an exploded view of the sensor illustrated in FIG. 1 and showing the components thereof.

With reference to FIGS. 1 and 2, the present invention, seen as an L-shaped oximeter sensor, is generally indicated by reference numeral 10. As seen in FIG. 2, the sensor 10 includes a flexible support structure 12, having inner and outer surfaces, 13a, 13b, respectively, a conformal adhesive tape laminate 14, and a removable liner 18, having opposed inner and outer surfaces, 19a, 19b, respectively. It is presently believed that the flexible support structure 12 be fabricated from a suitably flexible material, with medical 22.5 mil PVC foam tape, currently the preferred material. It is to be understood that any suitably flexible material may be used such as elastic woven fabric on a 5.5 mil latex free rubber based adhesive, as supplied by Scapa Tapes, or a combination of 3.6 mil clear plastic polyethylene medical tape and 6.6 mil transparent, perforated EVA medical tape, both supplied by 3M, by way of example. As may be further seen in FIG. 2, the sensor 10 additionally includes a leveling pad 20 including a notch 21 at one end, a light source 22, a photo-sensor 24 residing in the notch 21 of the leveling pad 20, and at least one positioning element 26. The adhesive tape laminate 14 is preferably a longitudinally folded structure and includes opposed top and bottom outer surfaces, seen as 15a and 15b, respectively. The adhesive tape laminate 14 further includes two facing, inner surfaces 17a, 17b, and a fold pocket area 16 located between the facing inner surfaces 17a, 17b. The light source 22, such as a light emitting diode (LED), and photodiode detector 24 are located between the facing inner surfaces 17, 17b of the conformal adhesive tape laminate 14 and in the fold pocket area 16 such that the light source 22 and the detector 24 are substantially opposed when the sensor 10 is in use. Lead wires 23 connect the light source 22 and the photo-detector 24 to a cable 25. A connector 29, attached to the other end of the cable 25, is configured to interface with a conventional oximeter box (not shown). The tape laminate 14 preferably includes an outer, light transmissive layer or coating 28, and at least one window area, 30. The window area 30 is an area of reduced thickness wherein a portion of an inner surface 17, 17b is removed, leaving only the outer, light transmissive coating 28. At least one of the optical elements, 22 or 24 extends inwardly of the window area 30 whereby light may pass through the window area 30. It is presently believed that the tape laminate be preferably formed from two adhered layers wherein one layer is formed from a medical 1.1 mil pearlized polypropylene tape, such as may be obtained from Scapa Tapes. The second layer is preferably formed from a medical 3.0/4.9 mil polyethylene film/double adhesive, as manufactured by 3M, by way of example.

Figure 4:
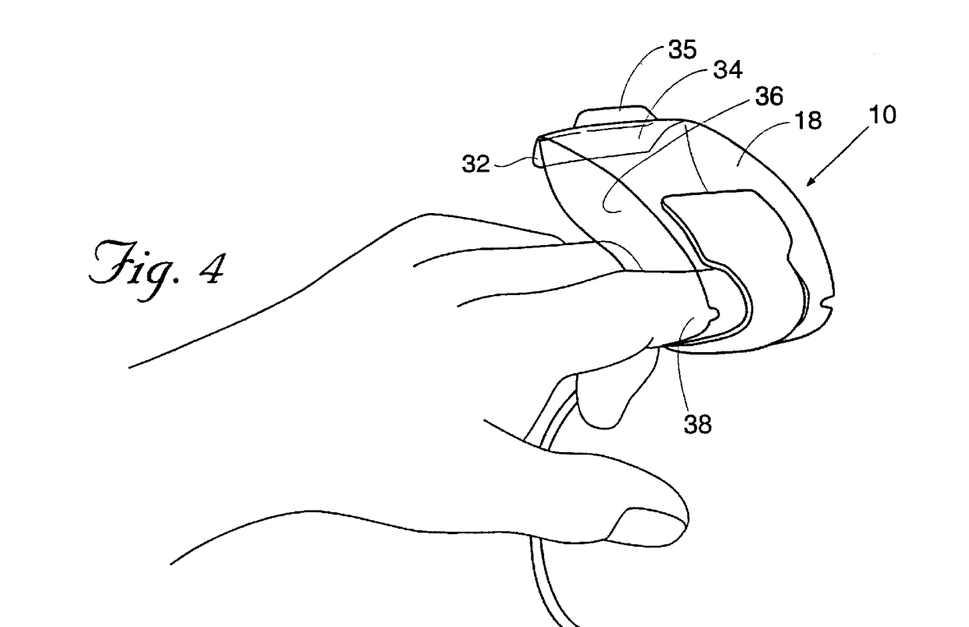
FIG. 4 is a perspective view of the novel sensor and showing pre-testing prior to removal of the transparent liner.

Further, the sensor 10 of the present invention is preferably releasably mounted on the removable liner 18. The liner 18 may be generally rectangularly shaped, and including an inner and an outer surface, 19a, 19b, respectively. The outer surface 19b adjoins the inner, adhesive surface 13a of the support structure 12. The outer surface 19b of the liner 18 is preferably coated with a non-stick agent, such as silicone, to allow facile removal from the support structure 12 at the time of use. It is presently believed preferable to form the removable liner 18 from 70 micron siliconized polypropylene film although it is to be understood that any other suitable material may be used, such as polyethylene. The removable liner 18 is further provided with a first end 32 and a second end 34. The ends, 32, 34 may be provided with means for temporary attachment to one another, such as the tongue 35 and slot 37 configuration shown in FIGS. 1, 2, and 4, seen particularly in FIG. 4. Prior to use and removal from the sensor support structure 12, the ends 32, 34 of the liner 18 may be connected to provide a pretesting tear drop area 36. The pretest tear drop 36 allows the light source 22 and photo sensor 24 to be positioned generally opposite each other. This allows for a quick pretest of the sensor 10 prior to mounting on a patient'appendage. As seen in FIG. 4, the pretest is accomplished by inserting an appendage (seen as a clinician'finger 38), temporarily, inside the tear drop 36 formed by the liner 18 so that it is positioned between the photo-sensor 24 and the light source 22. It is presently believed preferable that the removable liner 18 be substantially transparent to the interrogation wavelengths of the light source 22, which are preferably in the range of between 600 and 1000 nanometers. As mentioned earlier, the removable liner 18 is preferably composed of a plastic such as polypropylene, which will permit initial adhesion of the inner, adhesive surface 13a of the support structure 12 while permitting subsequent removal of the support structure 12 at time of use.

The sensor 10 of the present invention is further provided with internal leveling means, seen as leveling pad 20 in these views. The leveling pad 20 is preferably a thin, deformable material, such as PVC foam tape of a thickness approximately equal to the optical elements 22, 24. Currently, it is believed that a thickness of about 22.5 mil is preferable, but it is to be understood that any thickness approximating the thickness of the optical elements may be used. The leveling pad 20 is positioned in the fold pocket area 16 of the tape laminate 14, and is notched at 21 to substantially surround the photo-sensor 24. The leveling pad 20 causes the area surrounding the photo-sensor to be brought to the level of the protruding photo-sensor 24, thus allowing the sensor 10 to conformably match the contours of the appendage (such as the finger 38 seen in FIGS. 5–7). This feature reduces the protrusion of the photo-sensor 24 into the skin of the patient, and additionally improves the sealing of the skin to the photo sensor, 24 thereby reducing incident stray light that may produce extraneous signal.

Figure 3:
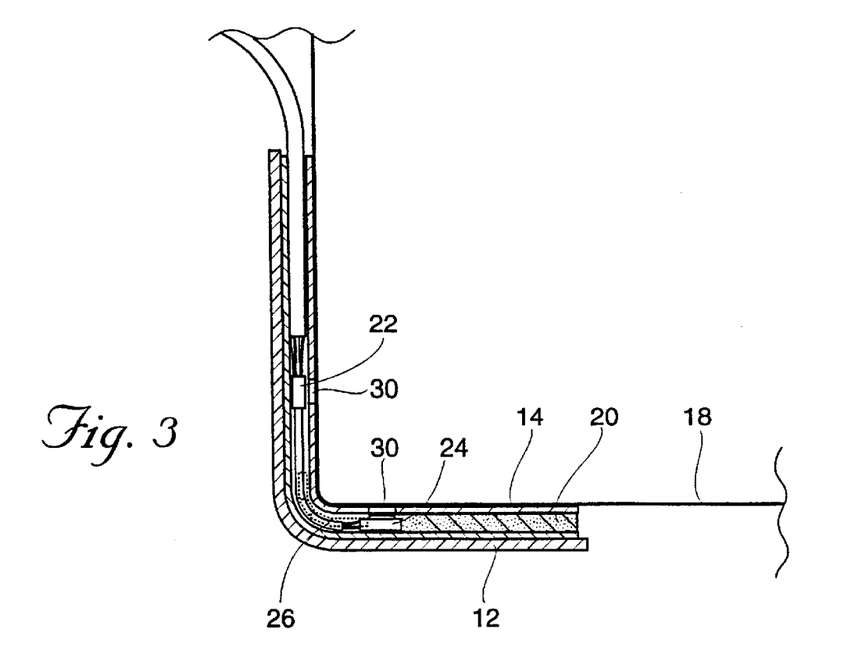
FIG. 3 is a cross sectional view of the sensor shown in FIG. 1 and taken along line 3—3 thereof.

As seen in FIGS. 2 and 3, the sensor 10 of the present invention is further provided with at least one positioning element, 26. The positioning element 26 is provided to cause the sensor 10 to maintain a generally L shape prior to use. The positioning element 26 is relatively stiff compared to the other layered elements 12, 14, and 18, and is preferably formed from polyester sheet stock of approximately 10 mil thickness. The positioning element is preferably scored slightly at 27 to provide the bend utilized to position the sensor 10 in a generally L shape. The positioning element 26 is preferably located in the fold pocket area 16 of the tape laminate 14 at a location approximately midpoint of the tape 14 longitudinal length, and preferably somewhat closer to the photo-sensor 24, thereby creating a sensor 10 having two leg portions 40a, 40b of unequal length. This configuration allows the clinician to position an appendage, such as a finger 38, up against the positioning element 26 (see FIG. 4).

Figure 5:
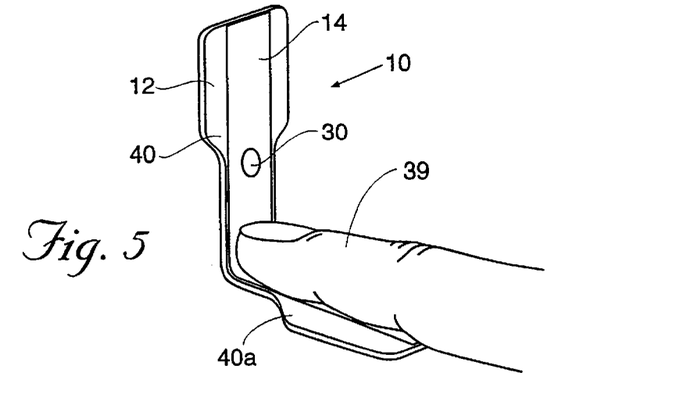
FIGS. 5–7, inclusive, are sequential views illustrating application of the sensor of the present invention to the finger of a patient.
Figure 6:
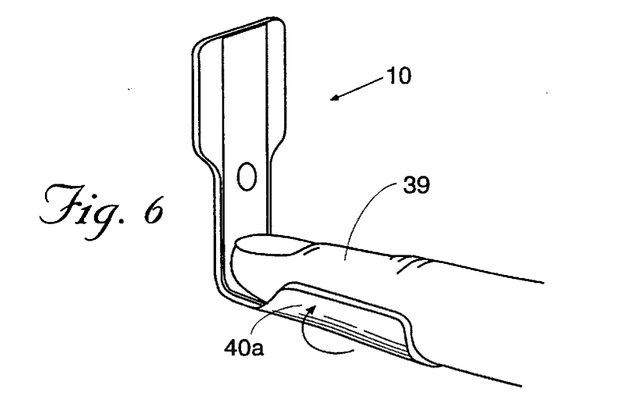
Figure 6A:
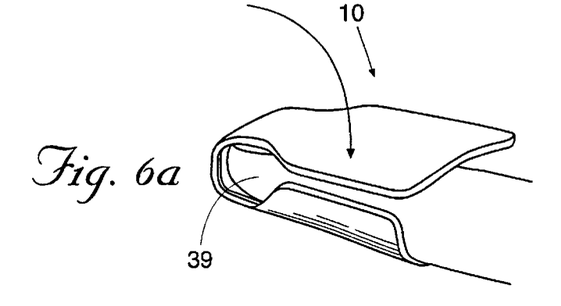
Figure 7:
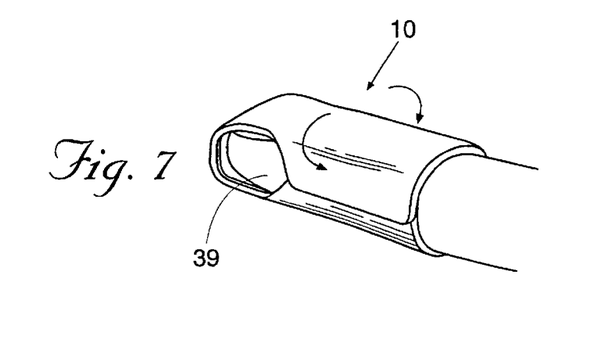

During application, the clinician bends the longer leg 40b, over the finger or other patient appendage 39, thereby easily and correctly positioning the optical elements 22, 24. Proper application of the sensor 10 to a patient appendage, such as a finger 39, is seen in the views of FIGS. 5–7.

Figure 8:
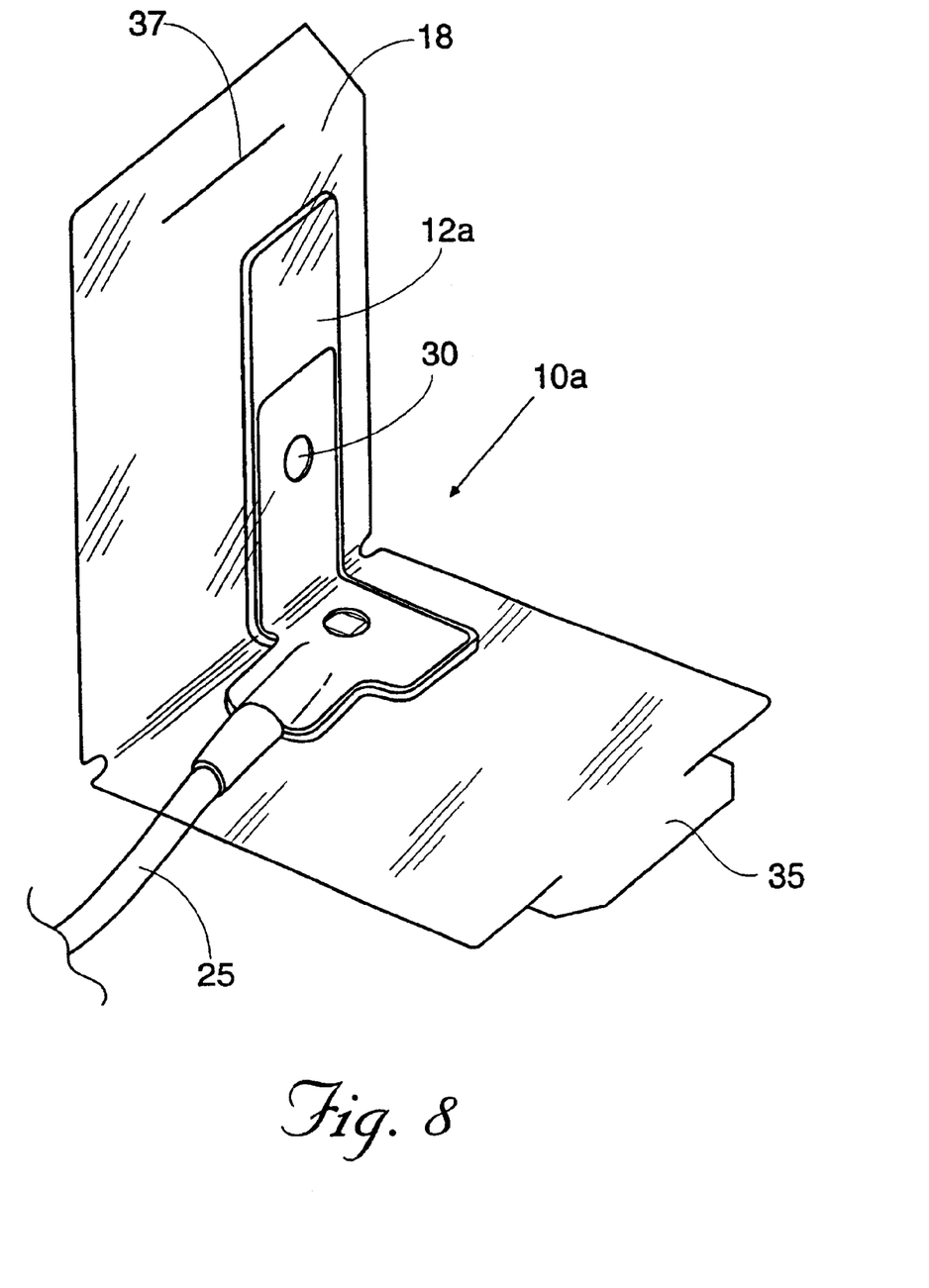
FIG. 8 is a perspective view of another embodiment of the novel oximeter sensor having particular neonatal application.

An alternate embodiment sensor 10 may be seen in FIG. 8. The embodiment 10a seen in FIG. 8 illustrates one configuration in which the elements of the present invention may be modified to present a sensor for use with neonates. As seen, the configuration of the support structure 12a is adapted to fit the foot (not seen) of a neonate, while presenting the sensor 10a in an initially L shape.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A non-invasive, electrooptical sensor probe for removable adhesive attachment to the skin of a patient for use in measuring light extinction during transillumination of the blood-perfused tissue beneath the skin, comprising:

a flexible, initially L-shaped web-like support structure containing substantially parallel, oppositely facing outer and inner surfaces, said inner surface including an adhesive coating;

a laminate tape structure containing a pair of longitudinally-spaced windows and being adhesively secured to said inner surface of said support structure;

a light source extending inwardly of one of said pair of windows being positioned to emit light;

a photo-sensor extending inwardly of the other of said pair of windows and being positioned to receive light emitted from said light source; and at least one positioning element being fabricated of a relatively stiff material sufficient to initially maintain a generally L shape to said supporting structure and to said adhering tape structure.

2. The non-invasive, electrooptical sensor probe of claim 1 wherein said L-shaped support structure includes integrally formed legs of unequal length.

3. The non-invasive, electrooptical sensor probe of claim 1 wherein said probe further includes a removable liner covering said outer surface of said support structure.

4. The non-invasive, electrooptical sensor probe of claim 1 further including a leveling pad structure including a notched end for receiving and surrounding said inwardly extending photo-sensor.

5. The non-invasive, electrooptical sensor probe of claim 1 wherein said laminate tape structure includes a first tape layer and a second tape layer and defining a pocket therebetween.

6. The non-invasive, electrooptical sensor probe of claim 5 wherein said positioning element is adhesively located in said pocket between said first and second tape layers.

7. The non-invasive, electrooptical sensor probe of claim 5 further including a leveling pad structure is adhesively located in said pocket between said first and second layers and arranged to minimize stray light received by said photo-senor.

8. The non-invasive, electrooptical sensor probe of claim 5 wherein said light source and said photo-sensor are each adhesively located in said pocket between said first and said second tape layers.

9. A method of pre-testing a non-invasive, electrooptical sensor probe comprising the steps of:

provinding a probe having a flexible, initially L-shaped, web-like, support structure containing substantially parallel, oppositely facing outer and inner surfaces, said inner surface including an adhesive coating, said probe further including a light source and a photo-sensor positioned to receive light emitted from said light source, and a removable liner covering said support structure and extending beyond said support structure to provide ends for temporary attachment to one another;

drawing said ends from said initial L shape towards one another;

temporarily attaching said ends together to form a tear drop loop therebetween; and temporarily inserting a blood-perfused portion of flesh for pre-testing measurement of light extinction.

\* \* \* \* \*